United States Patent [19]

Hagmann et al.

[11] Patent Number: 5,113,864
[45] Date of Patent: May 19, 1992

[54] ELECTRIC FIELD AND TEMPERATURE PROBE

[75] Inventors: Mark J. Hagmann, Miami; Tadeusz M. Babij, Fort Lauderdale, both of Fla.

[73] Assignee: Florida International University, Miami, Fla.

[21] Appl. No.: 188,043

[22] Filed: Apr. 29, 1988

[51] Int. Cl.⁵ ............................................. A61B 5/05
[52] U.S. Cl. ............................ 128/653.1; 128/736; 324/72.5
[58] Field of Search ............... 128/653 R, 736, 804; 324/72.5, 95, 106

[56] References Cited

U.S. PATENT DOCUMENTS

| | | | |
|---|---|---|---|
| 3,721,900 | 3/1973 | Andrews | 324/95 |
| 3,794,914 | 2/1974 | Aslan | 324/95 |
| 3,931,573 | 1/1976 | Hopfer | 324/95 |
| 4,091,327 | 5/1978 | Larsen et al. | 324/95 |
| 4,392,108 | 7/1983 | Hopfer | 324/95 |
| 4,588,993 | 5/1986 | Babij et al. | 343/351 |
| 4,813,429 | 3/1989 | Eshel et al. | 128/804 |

FOREIGN PATENT DOCUMENTS

| | | | |
|---|---|---|---|
| 425134 | 9/1974 | U.S.S.R. | 324/106 |
| 469929 | 11/1975 | U.S.S.R. | 324/106 |

OTHER PUBLICATIONS

R. R. Bowman "Some Recent Devt's in the Characterization and Measurement of Hazardous EM Fields", Biologic Effects and Health Hazards of MW Radiation, Polish Medical Publishers, Warsaw (1974), pp. 217–227.

R. R. Bowman, "A Probe for Measuring Temperature in RF Heated Material", IEEE, Transactions on MW Theory and Techniques, vol. MTT-24 (Jan. 1976), pp. 43–45.

Primary Examiner—Lee S. Cohen
Assistant Examiner—K. M. Pfaffle
Attorney, Agent, or Firm—Harry W. Barron

[57] ABSTRACT

A catheter is used to insert a probe into a tumor undergoing hyperthermia treatment. The probe is designed to isotropically measure the electric field and temperature in the tumor during the hyperthermia treatment. The probe is constructed on a triangular prism and includes a dipole on each prism face oriented at an angle of 54.74 degrees relative to the axis of the prism. Each dipole includes rectifier means therein and the three dipoles are coupled serially using high resistivity lead means. In addition, high resistivity leads are used to couple the dipoles to a high input impedance amplifier. A pair of thermistors are coupled between the three dipoles, and high resistance lead means couple the thermistors to high input impedance amplifiers. A current source is used to provide current to the thermistors in a time shared manner when the electric field is not being measured. The probe may have a pair of beryllium oxide or diamond layers attached to the ends thereof against which the thermistors may be positioned. With the above construction, the total electric field may be measured as well as the temperature at two locations.

25 Claims, 2 Drawing Sheets

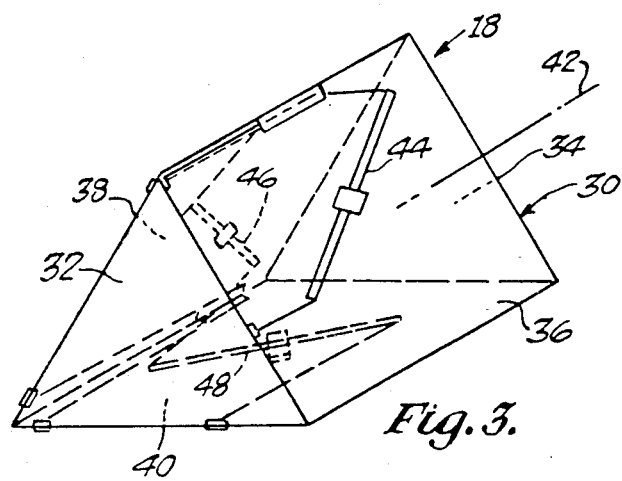
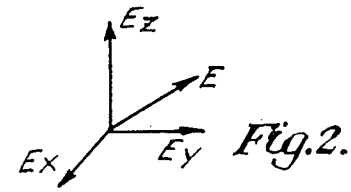
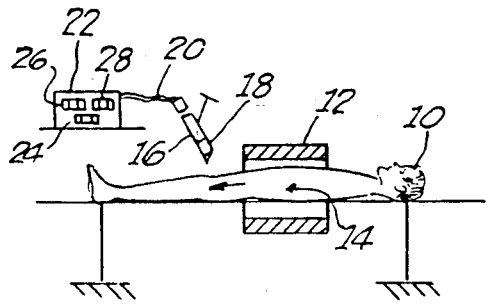
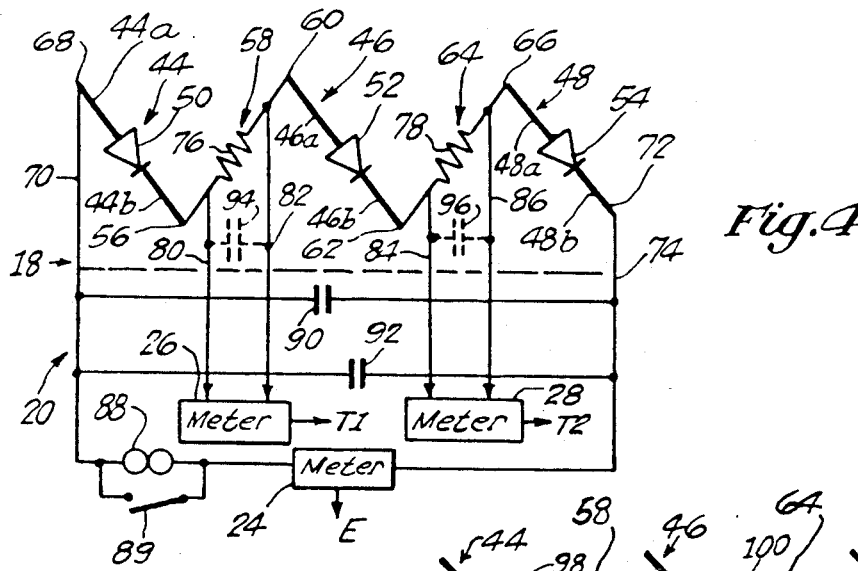
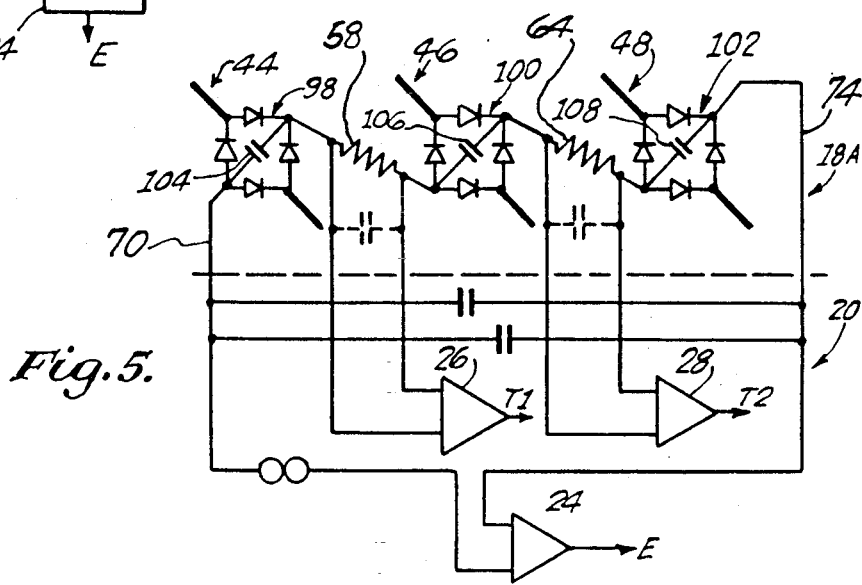

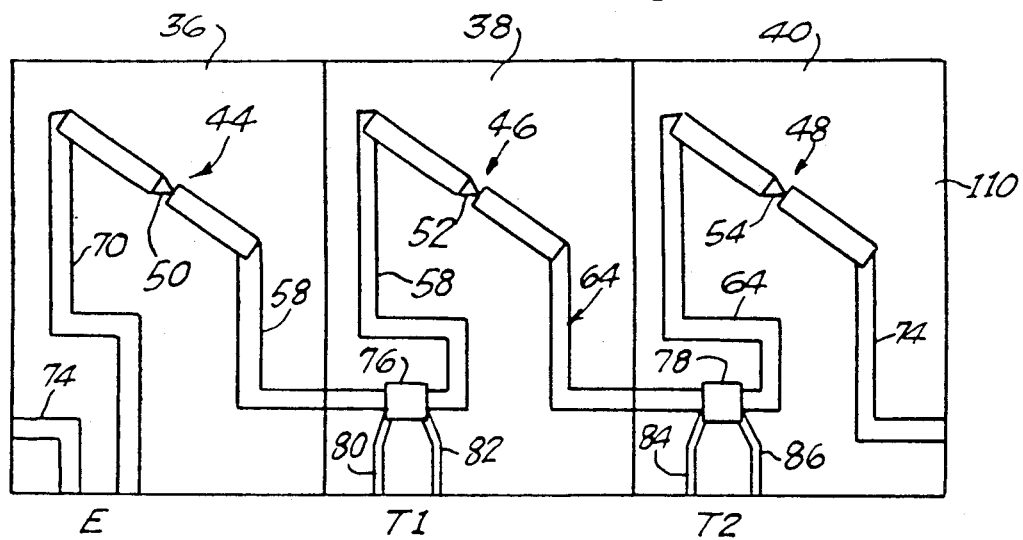
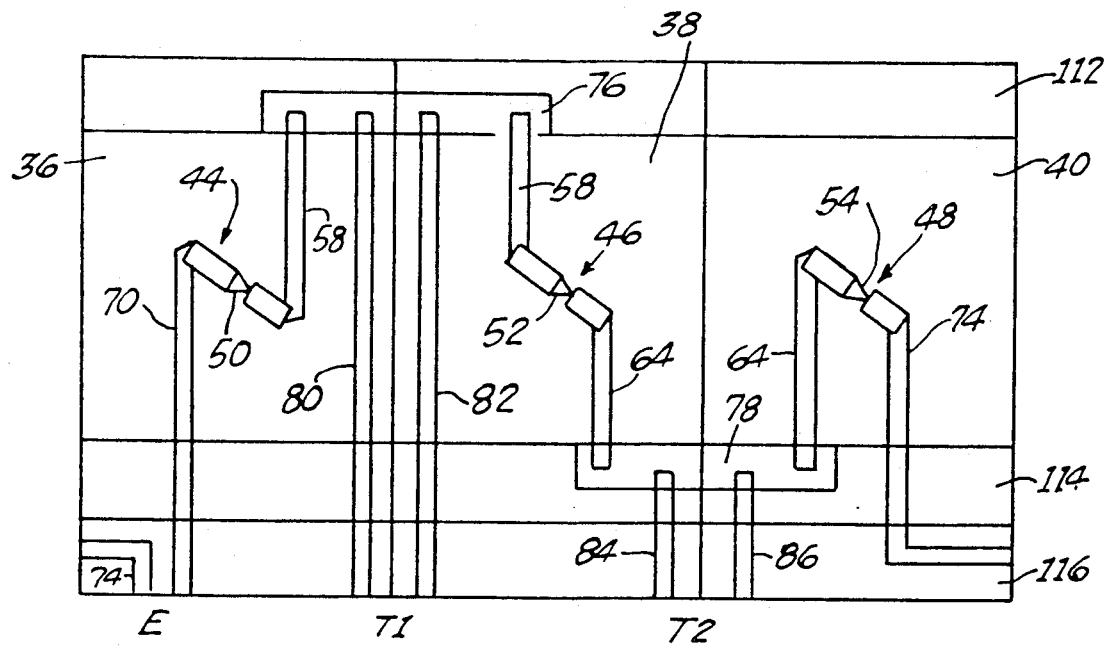

ELECTRIC FIELD AND TEMPERATURE PROBE

This invention relates to a probe for measuring an electric field and the ambient temperature within that field, and more particularly, to a miniature probe which is suitable for use for the invasive measurement of an electric field and ambient temperature within a human body being treated by hyperthermia.

In recent years hyperthermia has become an accepted treatment for certain types of cancerous tumors. One type of hyperthermia treatment and a device for performing hyperthermia treatment is described in U.S. Pat. No. 4,462,412 in the name of Turner and entitled "Annular Electromagnetic Radiation Applicator For Biological Tissue And Method". According to the teachings of this patent, electromagnetic energy is focused towards the tumor and causes the tumor to be heated to a certain temperature, for example, greater than 42° C. This focused electromagnetic field and associated heating of the tumor caused thereby results in destroying the tumor tissue.

One problem with the use of focused electromagnetic energy as a heating source for hyperthermia treatment is the difficulty in determining whether the energy is focused precisely at the desired spot, that is, the entire volume of the tumor. In the past, temperature sensitive probes have been inserted percutaneously through the skin into the tumor region to measure the temperature of the tumor and other tissue. The goal of hyperthermia treatment is to increase the temperature of the tumor tissue to a destruction temperature of approximately 42° C. and minimize the damage of nearby normal tissues. This goal is only realized if the energy field is focused within the tumor.

The temperature measurement technique of the prior art does not indicate the amount of the electromagnetic energy within the tumor. Further, there is a significant amount of time between the application of the energy to the tumor and the rise in temperature and the corresponding indication that the energy field is properly focused. Thus, the temperature measurement technique does not immediately manifest a situation where the hyperthermia device is not properly focused.

In addition, other problems exist when utilizing a temperature probe in a strong electromagnetic field area. If conductive leads, such as wires, are utilized, they act as antennas and become very hot, causing burns, particularly where the leads exit the body. To overcome this problem, systems have been described which utilize thermistors in conjunction with high resistance leads in place of the conducting wires. For example, see L. E. Larsen et al. "A Microwave Decoupled Brain-Temperature Transducer", IEEE "Transactions On Microwave Theory And Techniques", Vol MTT-22, pages 438-444 (April 1974) and R. R. Bowman, "A Probe For Measuring Temperature in Radio Frequency Heated Material", IEEE, "Transactions On Microwave Theory And Techniques", Volume MTT-24, pages 43-45 (January 1976). Other probes have been suggested using optical fiber technology, such as described in U.S. Pat. Nos. 4,136,566, 4,245,507 and 4,437,772. While the fiber optic temperature sensors have less of a problem of heating, they are less accurate and substantially more expensive than the temperature probes suggested by Larsen et al. and Bowman.

Another problem, regardless of the type of probe utilized in measuring the temperature within the tumor, is that the temperature tends to rise slowly compared to the almost instantaneous application of the electromagnetic field. Thus, a substantial time is required before the distribution of energy can be determined. It is preferable to measure the field itself directly rather than measuring the temperature as an indication of the field. However, there presently does not exist a probe for isotropically measuring an electric field which is small enough to be inserted into a catheter for subsequent insertion into the human body. As is well known, the electric field at a point is a vector having three components, such as in the X, Y and Z direction. In order to measure the entire electric field, it is necessary to measure the three X, Y, and Z components of that field.

Small electric field measuring probes, having a single dipole, which could be utilized in a catheter, have been constructed in the past. For example, see U.S. Pat. No. 4,642,558. However, with only a single dipole, only one component of the field can be measured, and this would provide misleading results, particularly since the orientation of the inserted dipole is not always the same, nor the same as the orientation of the field being measured. Similarly, probes suitable for isotropic measurements of electric fields are known, as indicated by U.S. Pat. Nos. 3,750,017 and 4,091,327. However, these probes are not suitable to be fabricated sufficiently small to be able to fit into a catheter. Further, they are not capable of being combined with apparatus suitable for measuring temperature at the same time as the electric field strength is measured.

While measuring the field strength is a better indication of the proper focusing of the hyperthermia device, it is desirable to still measure the temperature of the tumor. It is preferable, of course, to have a single probe which is capable of measuring both the three-dimensional electric field and the ambient temperature of the environment in which the probe is located. Even more advantageous would be the ability to measure the temperature at two or more remote points within the probe area. Significant additional information, useful to the clinician could be obtained by analyzing the time of the temperature rise for a constant known field.

In accordance with one aspect of this invention, there is provided an electric field probe for use with a high input impedance voltage meter for measuring the strength of an electrical field. The probe comprises three low resistivity dipole means positioned orthogonal to one another, each dipole means including first and second coupling terminals. In addition, the probe includes high resistivity interconnect lead means coupled from one terminal of a first one of a dipole means to one terminal of a second one of the dipole means and from the other terminal of the second dipole means to one terminal of a third one of the dipole means. Finally, the probe includes high resistivity meter lead means for coupling the other terminals of the first and third dipole means to the meter.

In accordance with another aspect of this invention there is provided a method of determining a property of a tumor having an electric field focused thereat causing the temperature thereof to increase. The method includes the steps of determining the electric field strength in, and temperature of, the tumor and determining the slope of the temperature verses time curve. In addition the method includes the step of determining the sign of the second derivative of the temperature verses time curve.

One preferred embodiment of the present invention is hereafter described, with specific reference being made to the following Figures, in which:

FIG. 1 shows a patient undergoing hyperthermia treatment and the probe system of the subject invention to be used in conjunction with such treatment;

FIG. 2 shows a vector diagram of the various directions of an electric field, E;

FIG. 3 shows how three dipoles and two thermistors used to isotropically measure the electric field strength and temperature may be arranged on a miniature probe;

FIG. 4 shows an electrical schematic diagram of one embodiment of the subject invention used for measuring the electric field strength and temperature;

FIG. 5 shows an electrical schematic diagram of a second embodiment of the subject invention used to measure electric field strength and temperature;

FIG. 6 shows one technique of layout for the various components used with the subject invention; and FIG. 7 shows an alternative technique of a layout for the various components of the subject inventions.

Referring now to FIG. 1, a patient 10 is undergoing treatment using an annular phased array hyperthermia unit 12 for destruction of a cancerous tumor 14. Annular phased array unit 12 may be similar to that manufactured by B.S.D. Medical Corporation of Salt Lake City, Utah, and is used to focus electromagnetic energy at tumor 14 for the purpose raising the temperature thereof to a therapeutic temperature.

In the treatment of cancer tumors by an annular phased array hyperthermia device, it is desirable to have a probe which can be inserted into the tumor for measuring both the field strength and the temperature of the tumor. Such a probe desirably is inserted percutaneously (through the skin) of patient 10 into tumor 14 by using a catheter holding the probe. A cable leading from the probe and catheter to instrumentation which records or displays both the field strength in and the temperature of tumor 14 is required. This cable must be miniaturized to fit within the catheter and not be of a type which acts as an antenna to pick up the energy from the field and thereby burn patient 10.

A catheter 16 is shown in FIG. 1 adapted to be inserted into tumor 14 and within the catheter 16 is a probe 18. Cable 20 extends from catheter 16 and is connected to meter 22, which includes electric field display 24 and temperature displays 26 and 28 for displaying respectfully the electric field and two different temperatures within tumor 14.

Referring now to FIG. 2, it is well known that an electric field E has three components referred to as Ex, Ey and Ez, oriented in the respective x, y and z directions. In order to determine the total electric field magnitude E ($E^2 = Ex^2 + Ey^2 + Ez^2$) using antenna dipoles, it is necessary to measure the three relative components Ex, Ey and Ez. In making these measurements, each of the dipoles must be aligned along one of the x, y or z axis in order to properly measure the field strength on that axis. Thus, probe 18 must be provided with three separate antenna dipoles, which are oriented perpendicular to one another, thereby defining the relative x, y, z axes. Without three such perpendicularly oriented dipoles, false readings of the total magnitude of the electric field E could result.

Referring now to FIG. 3, probe 18 is shown in a configuration useful for measuring both the magnitude of the total electric field Ex, Ey, Ez, as well as two temperature values in the tissue at two independent points, while at the same time being small enough to fit within the small inner diameter (approximately one millimeter) of catheter 16. Probe 18 includes a triangular prism 30 having two parallel triangular ends 32 and 34 and three rectangular faces 36, 38 and 40 between the ends 32 and 34. In order for probe 18 to fit within a one millimeter catheter 16 opening, the dimension of each of the sides of the triangular ends 32 and 34 should be in the order of 0.86 millimeter in length. While the distance separating the ends is not critical, it should not be more than approximately 4 to 5 millimeters. With these lengths, probe 18 may be placed in tumor 14 using a conventional catheter 16.

It is not practical, nor desirable, to place three dipoles required for obtaining an isotropic reading of an electric field along the x, y, and z axes having a common intersection point, such as shown in FIG. 2. Such a configuration requires more space than is available in fabricating probe 18 sufficiently small to fit within catheter 16. It also increases the cross talk between the lines connecting the three dipoles. It also is well known that the dipoles can be displaced from center axis 42 of a triangular configuration, such as prism 30, such that each of the dipoles is at an angle of 54.74 degrees with respect to center axis 42 in order to isotropically measure an electric field. For example, see R. R. Bowman, "Some Recent Developments In The Characterization and Measurement Of Hazardous Electromagnetic Fields", in Biologic Effects and Health Hazards of Microwave Radiation, Polish Medical Publishers, Warsaw (1974) pages 220-221. Accordingly, the three dipoles 44, 46 and 48 are placed on the three faces 36, 38 and 40 of prism 30 at an angle of 54.74 degrees with respect to axis 42. Additional elements, which are described hereafter with respect to FIGS. 4, 5, 6 and 7, are also placed on the faces 36, 38 and 40 of prism 30, together with interconnecting leads and connector elements used to couple the dipoles 44, 46 and 48 to cable 20.

Referring now to FIG. 4, each of the three dipoles 44, 46 and 48 are fabricated of a low resistivity material and divided into two arms, at the center thereof, by a rectifier means, such as diodes 50, 52 and 54 respectfully. Additionally, the three rectified dipoles 44, 46 and 48 are serially connected by high resistivity leads, such that the end 56 of dipole half 44b is coupled through high resistivity leads means 58 to end 60 of dipole half 46a and the end 62 of dipole half 46b is coupled through high resistivity leads means 64 to an end 66 of dipole half 48a. The other end 68 of dipole half 44a is coupled through high resistivity leads means 70 to meter 24 and the other end 72 of dipole half 48b is coupled through high resistivity lead means 74 to the other input of meter 24. Meter 24 may be any high input impedance voltage meter which provides a voltage E manifesting the strength of the electric field being measured. Each of the two dipole halves 44a and 44b, 46a and 46b, and 48a and 48b may be fabricated of a low resistivity material, such as copper or gold, and each of the high resistivity lead means 58, 64, 70 and 74 may be fabricated of a high resistivity material, such as carbon or other materials suitable for the thin-film or monolithic techniques used in fabrication.

In prior art isotropic electric field measuring probes, it is necessary to have two high resistivity leads from each dipole to the meter. Thus, for three dipoles, six leads are required; this, however, renders cable 20 too large and fragile, particularly if temperature measuring leads were also to be included therewith, as will be described hereafter. In order to reduce the number of leads, the diodes 50, 52 and 54 and high resistance interconnect leads 58 and 64 are provided and the diodes are electrically poled in the same direction. This permits the rectified outputs of the three dipoles 44, 46 and 48 to be combined through resistances large enough to provide radio frequency isolation between the dipoles 44, 46 and 48.

It should be recalled from FIG. 3 that each of the dipoles 44, 46 and 48 are positioned along one relatively defined x, y or z axis and that the square of the magnitude of the total electric field is the sum of the square of the components measured ($E^2 = Ex^2 + Ey^2 + Ez^2$ square-law) for each axis. The voltage between dipole sides 68 and 72 is the sum of the voltages across each of the dipoles 44, 46 and 48 and across each of the leads 58 and 64. Because of the high impedance of meter 24, the current is small so that the voltage drop across resistive leads 58 and 64 is negligible. Since the dipoles 50, 52 and 54 operate in the square-law region, the voltage from each diode is proportioned to the square of the electric field parallel to respective dipole. Thus, the square of the magnitude of the total electric field may be determined by the voltage drop between the sides 68 and 72. Alternatively, inductors could replace the high resistivity leads 58 and 64, but the fabrication of inductors by semiconductor techniques is very difficult and not susceptible to miniaturization. Further, a broad band probe can not be built using inductors due to the large variation of reactance with different frequencies.

High resistivity leads 70 and 74 are coupled to high resistivity leads within cable 18 which in turn are coupled to meter 24. As previously mentioned, meter 24 must have a high input impedance so that the large, but variable, resistances of leads 58 and 64 do not effect the accuracy of voltage measurements, particularly where a thermistor is included with the leads 58 and 64 to measure temperature, as described below.

In order to utilize probe 18 as a temperature measuring device in addition to an electric field measuring device, a pair of thermistors 76 and 78 are included as a part of each high resistivity leads means 58 and 64. In addition, high resistivity leads 80 and 82 and 84 and 86 are coupled from both sides of thermistors 76 and 78 respectively to meters 26 and 28. In addition, a current source 88 is provided to ensure that a constant current flows through thermistors 76 and 78. Current source 88 may be time shared in that it only operates while temperature readings are being made so that it does not interfere with the field measurements. This is manifested by switch 89.

As is well it is well known, a thermistor has resistance which varies with respect to the temperature surrounding that element. Thus, as the temperature rises within tumor 14, the resistance of thermistors 76 and 78 will vary. Thus, as the constant current from current source 88 is provided through thermistors 76 and 78, the voltage thereacross will vary with the change in resistance due to the change in temperature. This voltage is measured by meters 26 and 28, which may have high input impedance amplifiers, and the output from meters 26 and 28 will thereby manifest the temperature sensed by the thermistors 76 and 78.

Capacitors 90 and 92 are coupled between high resistivity leads 70 and 74 to serve as a filter in the electric field measurement, and capacitors 94 and 96 are provided between respective leads pairs 80 and 82 and 84 and 86 to prevent RF heating of thermistors 76 and 78.

Capacitors 94 and 96 may be the inherent line capacitance between leads 80 and 82 or between leads 84 and 86, particularly where semiconductor fabrication methods, such as thin film or thick film techniques are utilized. Alternatively, capacitors 94 and 96 may be minature discreet components.

Referring now to FIG. 5, a probe 18A is shown which differs only from the embodiment of FIG. 4 in that the diodes 50, 52 and 54 are replaced with full wave rectifiers 98, 100 and 102. Where appropriate, like numerical designations are given for like components. Each full wave rectifier 98, 100 and 102 includes four diodes connected in a bridge configuration. The two terminals of a bridge in which a diode anode and cathode are coupled together are connected to the arms of the respective dipoles 44, 46 and 48. The opposite two terminals of the bridge configuration, in which either two anodes or two cathodes are coupled together, serve as the terminal to which leads 58, 64, 70 and 74 are coupled. In addition, capacitors 104, 106 and 108 are coupled across the terminals of the rectifiers 98, 100 and 102.

Other configurations of the rectified dipoles 44, 46 and 48 are also possible. The important consideration is that the three mutually orthogonal dipole antennas 44, 46 and 48 have a d.c. output which can be added between the leads 70 and 74. In other words, the intent is to combine the rectified outputs of the three dipoles 44, 46 and 48, such that the high resistance value of the leads 58 and 64 provide RF isolation between each of the antennas 44, 46 and 48.

Referring now to FIGS. 6 and 7, examples of the manner in which the various components described above with respect to FIGS. 3 and 4 are physically positioned are given. In FIG. 6 and 7, the components may be fabricated directly on a silicon or gallium arsenide semiconductor substrate forming prism 30, shown in FIG. 3, or may be fabricated by thin film or thick film technique on a Kapton or other dielectric film which is later applied over a glass, or other inert material substrate, in the form of prism 30.

Referring specifically to FIG. 6, the three dipoles 44, 46 and 48 are fabricated on a Kapton film 110 by known thin film technique. The material of each of the dipole halves of dipoles 44, 46 and 48 may have a low resistivity, such as copper or gold. Alternatively, any material having a resistivity below 10 micro-ohm meters may be used. For high frequency response, it is desirable to use high-resistivity dipoles with approximately 1 ohm-meter. Each of the dipoles 44, 46 and 48 are positioned at 54.74 degrees with respect to the vertical as seen in FIG. 6. Between each of the dipole arms diodes 50, 52 and 54 are coupled in circuit with the dipole halves. Diodes 50, 52 and 54 may preferably be zero biased beam lead Schottky diodes, which are generally preferred detectors for low level RF signals. For example, Hewlett Packard model 5082-2837 diodes may be used in the FIG. 4 configuration or model 5082-9394 quad diodes may be used in the FIG. 5 configuration.

Connected to each end of dipoles 44, 46 and 48 are high resistivity leads 70, 58, 64 and 74. The high resistivity leads 70, 58, 64 and 74 material may be carbon-loaded Teflon, which has a resistivity of approximately 1 ohm-meter. Alternatively, any material having a resistivity above at least 1000 times that of the material used for dipoles may be used so long as the resistivity of leads 70, 58, 64 and 74 is sufficient to minimize the perturbation of the electric field being measured, and that of leads 58 and 64 is sufficient to decouple the radio frequency voltage of the dipoles.

Connected between the two lines forming high resistivity leads 58 and 64 are thermistors 76 and 78, which are suitable for hybrid construction. Examples of suitable thermistors are the "Thermo Flake" thermistors manufactured by Thermometrics of Edison, N.J. Alternatively, thermistors may be fabricated using monolithic techniques. The leads 80 and 82 and 84 and 86, extending from thermistors 76 and 78 are of similar high resistivity material as the leads 70, 58, 64 and 74 discussed above.

In physical size, the overall length of each of the dipoles 44, 46 and 48 should be approximately 1.0 millimeter and the width of each of the leads 58, 64, 70, 74, 80, 82, 84 and 86 should be approximately 0.10 millimeter. The overall width of each of the panels corresponding to the faces 36, 38 and 40 of prism 30 are approximately 0.86 millimeter. The overall length of each of the panels corresponding to the faces 36, 38 and 40 is approximately 2 millimeters. The above dimensions are suitable for construction of a probe which is small enough to fit into a catheter 16 having an inside diameter of 1.2 millimeters. In many applications it is unnecessary to construct an electric field meter as small as the one required for inclusion in catheter 16. In those circumstances, the dimensions given above may be many times those exemplified. However, the length of the dipoles is generally less than one-half of the wavelength of the electric field being measured.

Referring now to FIG. 7, an alternate embodiment of a layout compared to the FIG. 6 embodiment layout is shown. Only the differences will be discussed and like numerical references are given for the equivalent components. In the FIG. 7 embodiment, beryllium oxide or diamond layers 112 and 114 are placed on the two ends 32 and 34 of prism 30. It is well known that beryllium oxide and diamond are dielectric materials that have an unusual combination of properties, in that they have a high thermal conductivity and low dielectric loss. Thus, where one places the thermistors 76 and 78 in physical contact with the beryllium oxide or diamond layers 112 and 114, the high thermal conductivity property of the materials cause the thermistors 76 and 78 to reach a mean temperatures at two different and separated locations within tumor 14. Layers 112 and 114 may be circular, rather than triangular in order to permit probe 18 to slide more easily into and out of catheter 16. Because of the low dielectric loss of the beryllium oxide or diamond layers 112 and 114, they suffer very little RF heating in the electric field being measured. In addition, on the back end of probe 18 a connector strip 116 is provided to which the leads 74, 80, 82 and 86 extend and may be coupled more easily to cable 20.

It is well known that tumors may be heterogeneous in composition. By knowing the electric field and the manner in which the temperature increases within the tumor, the clinician may be provided with additional information about the treatment that has not heretofore been available. For example, the ratio of the square of the electric field strength to the derivative of the change of the temperature over time is proportional to $\sigma/pc$ where $\sigma$ is electrical conductivity, p is density, and c is the specific heat, all properties of the tissue. Thus, information regarding the tissue composition may be obtained during the treatment. Also, by calculating the second derivative of the change of the temperature over time, one may determine whether the region of measurement is hot or cold relative to the surrounding tissue. This latter information is useful to the clinician when determining whether the electromagnetic field is properly focused at the desired area.

Referring again to FIG. 1, in using probe 18, it may be inserted into tumor 14 prior to the positioning of patient 10 in hyperthermia apparatus 12. After patient 10 is properly positioned with respect to apparatus 12, the initial focusing of the electromagnetic field is accomplished by maximizing, the electric field strength of the field at tumor 14, as read by meter 24. At the same time, a continual reading over time of the rise in temperature is read from meters 26 and 28. The first derivative of temperature versus time, that is the rate of temperature rise, is then determined. The ratio of the square of the electric field strength to the first derivative of temperature versus time serves as an indication of the type of tissue undergoing treatment.

When the tissue type is generally known, a slower rise of the temperature than expected is an indication that apparatus 12 is not properly focused. After the initial temperature versus time slope is determined, the second derivative of the temperature verses time curve may be determined. If this is less than zero, the tumor 14 in which probe 18 is inserted is a localized "hot spot", which is the desired response, and if the second derivative is greater than zero, the tumor 14 in which probe 18 is inserted is a localized "cold spot", therefore indicating that the field strength from apparatus 12 is either insufficient for treatment or not properly focused. The accuracy of these measurements is increased when both temperature and electric field strength are measured simultaneously at the same location. Thus, probe 18 is ideal for providing additional information.

Probe 18 may also be used during the initial focusing of energy from applicator 12 to assist the clinician. During initial focusing, the power of the signal provided by the applicator is maintained at the low value so that no healthy tissue will be destroyed. With probe 18 inserted in tumor 14, the focus of applicator 12 is adjusted until a maximum electric field reading is manifested by meter 26. Thereafter, full power electromagnetic energy may be provided by applicator 12.

What is claimed is:

1. An electric field sensing probe for use with a high input impedance voltage meter for measuring the strength of an electric field, said probe comprising:

a triangular prism;

three low resistivity dipoles positioned orthogonal to one another, each of said dipoles being positioned on a different one of the sides of said prism, each of said dipoles including first and second coupling terminals;

high resistivity interconnect lead means for coupling one terminal of a first one of said dipoles to one terminal of a second one of said dipoles and for further coupling the other terminal of said second dipole to one terminal of a third one of said dipoles; and high resistivity meters lead means for coupling the other terminals of said first and third dipoles to said meter.

2. The invention according to claim 1 further including said meter for detecting and displaying a voltage applied thereto from said meter lead means as a manifestation of the strength of said field.

3. The invention according to claim 1 wherein the ratio of the length of each dipole to the wavelength of the field being measured is less than one-half.

4. The invention according to claim 3 wherein each of said dipoles includes means for rectifying.

5. The invention according to claim 4 wherein said terminals are remote from said means for rectifying.

6. The invention according to claim 4 wherein said means for rectifying is a diode positioned midway between said terminals.

7. The invention according to claim 4 wherein said means for rectifying includes said terminals.

8. The invention according to claim 4:
wherein each of said dipoles include first and second dipole arms; and
wherein said means for rectifying is a full wave rectifier positioned between said dipole arms.

9. The invention according to claim 1 wherein each of said dipole means includes means for rectifying.

10. The invention according to claim 9 wherein said terminals are remote from said means for rectifying.

11. The invention according to claim 9 wherein said means for rectifying is a diode positioned midway between said terminals.

12. The invention according to claim 9 wherein said means for rectifying includes said terminals.

13. The invention according to claim 9:
wherein each of said dipoles include first and second dipole arms; and
wherein said means for rectifying is a full wave rectifier positioned between said dipole arms.

14. The invention according to claim 1:
wherein said triangular prism is an equilateral triangular prism; and
wherein each of said dipoles includes a dipole element positioned on the face of the said prism at an angle of 54.74 degrees with respect to the axis of said prism.

15. The invention according to claim 14 wherein said interconnect lead means and said meter lead means are positioned on said prism faces.

16. An electric field and temperature sensing probe for being coupled to a first high input impedance voltage meter for measuring the strength of an electric field and for being coupled to a second high input impedance voltage meter for measuring the temperature of the environment of said field, said probe comprising:
three low resistivity dipoles positioned orthogonal to one another, each dipole including first and second coupling terminals;
high resistivity interconnect lead means, including a thermistor, for coupling one terminal of a first one of said dipoles to one terminal of a second one of said dipoles and for further coupling the other terminal of said second dipole to one terminal of a third one of said dipoles;
first high resistivity detector lead means for coupling the other terminals of said first and third dipoles to said first meter and
second high resistivity detector lead means for coupling said thermistor to said second meter.

17. The invention according to claim 16 wherein said probe further includes time shared current source means for providing a constant current through said first high resistivity meter lead means during the time said temperature is being measured.

18. The invention according to claim 17
wherein said probe includes a triangular prism; and
wherein said three low resistivity dipoles are positioned on the faces of said triangular prism at an angle of 54.74 degrees with respect to the axis of said prism.

19. The invention according to claim 18 wherein each of said dipoles includes means for rectifying.

20. The invention according to claim 19 wherein the resistivity of each of said interconnect lead means, said first lead means and said second lead means is at least one thousand times greater than the resistivity of said dipoles.

21. The invention according to claim 16 wherein the resistivity of each of said interconnect lead means, said first lead means and said second lead means is at least one thousand times greater than the resistivity of said dipoles.

22. An electric field and temperature measuring device for measuring an electric field magnitude at a certain location, there being an ambient temperature at said location, said device further measuring the ambient temperature at said location, said device comprising:
a substrate containing first means for providing a first signal manifesting the electric field magnitude and second means for providing a second signal manifesting the ambient temperature;
first means to which said first signal is applied for displaying a manifestation of said electric field magnitude; and
second means to which said second signal is applied for displaying a manifestation of said temperature.

23. The invention according to claim 22 wherein said first means includes three orthogonally positioned and electrically conductive and serially coupled elements and said second means is electrically coupled between at least two of said conductive elements.

24. The invention according to claim 23 wherein said substrate is a triangular prism and said first means includes said three elements, each positioned respectively on a different face of said prism.

25. The invention according to claim 22 wherein said substrate is a triangular prism and said first means includes three elements, each positioned respectively on a different face of said prism.

* * * * *